United States Patent [19]

Staudenmayer et al.

[11] Patent Number: 4,746,741

[45] Date of Patent: May 24, 1988

[54] N,N'-BIS[2-(3-METHYLPHENYL)ETHYL]-PERYLENE-3,4:9,10-BIS (DICARBOXIMIDE) COMPOUND USE THEREOF IN MULTI-ACTIVE PHOTOCONDUCTIVE INSULATING ELEMENTS EXHIBITING FAR RED SENSITIVITY

[75] Inventors: William J. Staudenmayer, Pittsford; Michael T. Regan, Fairport, both of N.Y.

[73] Assignee: Eastman Kodak Company, Rochester, N.Y.

[21] Appl. No.: 67,337

[22] Filed: Aug. 14, 1987

Related U.S. Application Data

[62] Division of Ser. No. 875,915, Jun. 19, 1986.

[51] Int. Cl.$^4$ .......... C07D 471/06

[52] U.S. Cl. .......... 546/37

[58] Field of Search .......... 546/37

[56] References Cited

U.S. PATENT DOCUMENTS

| | | | |
|---|---|---|---|
| 3,871,882 | 3/1975 | Wiedemann | 430/59 |
| 3,904,407 | 11/1975 | Regensburger et al. | 430/58 |
| 4,156,757 | 5/1979 | Graser et al. | 428/411 |
| 4,419,427 | 12/1983 | Graser-et al. | 430/58 |
| 4,429,029 | 1/1984 | Hoffmann et al. | 430/57 |
| 4,514,482 | 4/1985 | Loutfy et al. | 430/78 |
| 4,517,270 | 5/1985 | Graser et al. | 430/58 |
| 4,578,334 | 3/1986 | Borsenberger et al. | 430/59 |

FOREIGN PATENT DOCUMENTS 3684955 3/1980 Japan .

*Primary Examiner*—Donald G. Daus
*Assistant Examiner*—William A. Teoli, Jr.
*Attorney, Agent, or Firm*—Alfred P. Lorenzo

[57] ABSTRACT

Multi-active photoconductive insulating elements which are sensitive in the far red region of the spectrum are comprised of a charge-generation layer and a charge-transport layer in electrical contact therewith and contain, as the charge-generating agent within the charge-generation layer, the compound N,N'-bis[2-(3-methylphenyl)ethyl]perylene-3,4:9,10-bis(dicarboximide). The charge-generation layer is capable, upon exposure to activating radiation, of highly effective generation and injection of charge carriers and the charge-transport layer, which is comprised of an organic composition containing an organic photoconductive material, is capable of accepting and transporting the injected charge carriers to thereby form a highly advantageous multi-active photoconductive insulating element.

1 Claim, No Drawings

N,N'-BIS[2-(3-METHYLPHENYL)ETHYL]-PERYLENE-3,4:9,10-BIS (DICARBOXIMIDE) COMPOUND USE THEREOF IN MULTI-ACTIVE PHOTOCONDUCTIVE INSULATING ELEMENTS EXHIBITING FAR RED SENSITIVITY

This is a division of application Ser. No. 875,915, filed June 19, 1986.

FIELD OF THE INVENTION

This invention relates in general to electrophotography and in particular to a novel perylene compound that is useful as a charge-generating agent in multi-active photoconductive insulating elements which are employed in electrophotography. More specifically, this invention relates to a novel perylene compound and to novel multi-active photoconductive insulating elements containing such compound which exhibit sensitivity in the far red region of the spectrum.

BACKGROUND OF THE INVENTION

Electrophotographic imaging processes and techniques have been extensively described in both the patent and other literature, for example, U.S. Pat. Nos. 2,221,776; 2,277,013; 2,297,691; 2,357,809; 2,551,582; 2,825,814; 2,833,648; 3,220,324; 3,220,831; 3,220,833 and many others. Generally, these processes have in common the steps of employing a photoconductive insulating element which is prepared to respond to imagewise exposure with electromagnetic radiation by forming a latent electrostatic charge image. A variety of subsequent operations, now well-known in the art, can then be employed to produce a permanent record of the charge image.

Various types of photoconductive insulating elements are known for use in electrophotographic imaging processes. In many conventional elements, the active components of the photoconductive insulating composition are contained in a single layer composition. This layer is coated on a suitable electrically-conductive support or on a non-conductive support that has been overcoated with an electrically-conductive layer.

Among the many different kinds of photoconductive compositions which may be employed in typical single-active-layer photoconductive elements are inorganic photoconductive materials such as vacuum-deposited selenium, particulate zinc oxide dispersed in a polymeric binder, homogeneous organic photoconductive compositions composed of an organic photoconductor solubilized in a polymeric binder, and the like.

Other especially useful photoconductive insulating compositions which may be employed in a single-active-layer photoconductive element are the high-speed heterogeneous or aggregate photoconductive compositions described in Light, U.S. Pat. No. 3,615,414 issued Oct. 26, 1971 and Gramza et al, U.S. Pat. No. 3,732,180 issued May 8, 1973. These aggregate-containing photoconductive compositions have a continuous electrically-insulating polymer phase containing a finely-divided, particulate, co-crystalline complex of (i) at least one pyrylium-type dye salt and (ii) at least one polymer having an alkylidene diarylene group in a recurring unit.

In addition to the various single-active-layer photoconductive insulating elements, such as those described above, various multi-active photoconductive insulating elements, that is, elements having more than one active layer, are also well known and, in general, are capable of providing superior performance. In such multi-active elements, at least one of the layers is designed primarily for the photogeneration of charge carriers and at least one other layer is designed primarily for the transportation of these charge carriers.

A particularly important class of charge-generating agents for use in multi-active photoconductive insulating elements is the class of perylene compounds. Thus, it is known in the prior art that the perylenes are capable of providing exceptional performance and many proposals have been made heretofore for the use of perylenes of widely varying structure. Most typically, the perylenes which are described as being especially useful in electrophotography are diimides characterized by the generic formula:

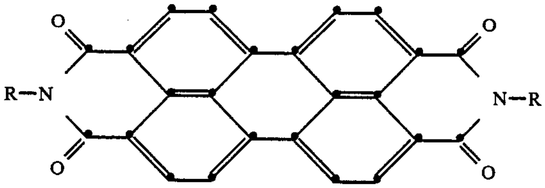

Representative examples of the many patents describing the use of perylenes of the above formula in multi-active photoconductive insulating elements include the following:

U.S. Pat. No. 3,871,882 to Wiedemann, issued Mar. 18, 1975, in which R is hydrogen, alkyl, aryl, aralkyl, a heterocyclic group or —$NHR^1$ in which $R^1$ is phenyl or benzoyl.

U.S. Pat. No. 3,904,407 to Regensburger et al, issued Sept. 9, 1975, in which R is alkyl, aryl, alkylaryl, alkoxyl, halogen or a heterocyclic group.

U.S. Pat. No. 4,156,757 to Graser et al, issued May 29, 1979, in which R is hydrogen, alkyl, oxaalkyl, cycloalkyl, alkaryl, aryl, halogen, nitro, amino or hydroxyalkyl.

Japanese Patent Publication No. 36849/55 assigned to Ricoh Company Ltd., published Mar. 14, 1980, in which R is hydrogen, aryl, alkyl, alkylaryl, halogen or a heterocyclic group.

U.S. Pat. No. 4,419,427 to Graser et al, issued Dec. 6, 1983, in which R is a 2,6-dichlorophenyl group.

U.S. Pat. No. 4,429,029 to Hoffman et al, issued Jan. 31, 1984, in which R is hydrogen, alkyl, aralkyl, aryl or alkylaryl and the aromatic skeleton is halogen-substituted to an extent of at least 45 percent.

U.S. Pat. No. 4,514,482 to Loutfy et al, issued Apr. 30, 1985, in which R is a trialkyl- or triaryl-substituted phenyl group.

U.S. Pat. No. 4,517,270 to Graser et al, issued May 14, 1985, in which R is propyl, hydroxypropyl, methoxypropyl or phenethyl.

U.S. Pat. No. 4,578,334 to Borsenberger et al, issued Mar. 25, 1986, in which R is a 2-phenethyl group.

While many different perylenes have been disclosed in the prior art to be useful in multiactive photoconductive insulating elements, they typically lack sensitivity in the far red region of the spectrum, i.e., in the region of from 650 to 700 nm. This is a very serious disadvantage as regards use of the photoconductive elements in devices such as electronic printers in which the exposure devices are typically lasers or light emitting diodes that emit in the far red.

It is toward the objective of overcoming the aforesaid disadvantage of known multi-active photoconductive insulating elements comprising perylenes that the present invention is directed.

SUMMARY OF THE INVENTION

It has now been found, most unexpectedly, that a very high degree of sensitivity in the far red is provided by the perylene compound N,N'-bis[2-(3-methylphenyl-)ethyl]perylene-3,4:9,10-bisdicarboximide, hereinafter referred to as 3-methyl PPC. This compound is of the generic formula given above in which each R is

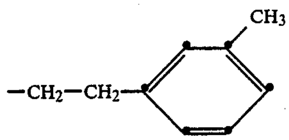

and thus has the specific formula:

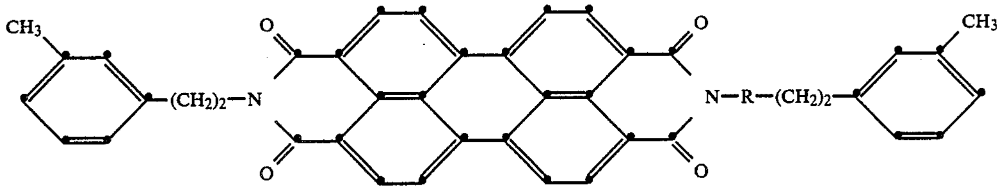

Perylene compounds of very similar structure to the novel perylene compound of this invention have been found to lack sensitivity in the far red region of the spectrum, and thus to be ineffective in applications such as electronic printers in which exposure is carried out with a laser or light emitting diode that emits in the far red. Both the novel compound itself and its use as a charge-generating agent in multi-active photoconductive insulating elements are encompassed within the scope of the present invention.

DESCRIPTION OF THE PREFERRED EMBODIMENTS

The novel multi-active photoconductive insulating elements of this invention have at least two active layers, namely a charge-generation layer in electrical contact with a charge-transport layer. The charge-generation layer is capable, upon exposure to activating radiation, of generating and injecting charge carriers into the charge-transport layer. The charge-transport layer is an organic composition comprising, as a charge-transport agent, an organic photoconductive material which is capable of accepting and transporting injected charge carriers from the charge-generation layer.

The term "activating radiation" as used herein is defined as electromagnetic radiation which is capable of generating electron-hole pairs in the charge-generation layer upon exposure thereof.

The charge-generation and charge-transport layers are typically coated on an "electrically-conductive support", by which is meant either a support material which is electrically-conductive itself or a support material comprised of a non-conductive substrate coated with a conductive layer. The support can be fabricated in any suitable configuration, such as that of a sheet, a drum or an endless belt. Exemplary "electrically-conductive supports" include paper (at a relative humidity above 20 percent); aluminum-paper laminates; metal foils such as aluminum foil, zinc foil, etc.; metal plates or drums, such as aluminum, copper, zinc, brass and galvanized plates or drums; vapor deposited metal layers such as silver, chromium, nickel, aluminum and the like coated on paper or conventional photographic film bases such as cellulose acetate, poly(ethylene terephthalate) polystyrene, etc. Such conducting materials as chromium, nickel, etc., can be vacuum deposited on transparent film supports in sufficiently thin layers to allow electrophotographic elements prepared therewith to be exposed from either side of such elements. An especially useful conducting support can be prepared by coating a support material such as poly(ethylene terephthalate) with a conducting layer containing a semiconductor dispersed in a resin. Such conducting layers, both with and without electrical barrier layers, are described in U.S. Pat. No. 3,245,833 by Trevoy, issued Apr. 12, 1966. Other useful conducting layers include compositions consisting essentially of an intimate mixture of at least one inorganic oxide and from about 30 to about 70 percent by weight of at least one conducting metal, e.g., a vacuum-deposited cermet conducting layer as described in Rasch, U.S. Pat. No. 3,880,657, issued Apr. 29, 1975. Likewise, a suitable conducting coating can be prepared from the sodium salt of a carboxyester lactone of maleic anhydride and a vinyl acetate polymer. Such kinds of conducting layers and methods for their optimum preparation and use are disclosed in U.S. Pat. Nos. 3,007,901 by Minsk, issued Nov. 7, 1961 and 3,262,807 by Sterman et al, issued July 26, 1966.

The charge-transport layer utilized in the elements of this invention can include a very wide variety of organic materials which are capable of transporting charge carriers generated in the charge-generating layer. Most charge transport materials preferentially accept and transport either positive charges (holes) or negative charges (electrons), although there are materials known which will transport both positive and negative charges. Transport materials which exhibit a preference for conduction of positive charge carriers are referred to as p-type transport materials, whereas those which exhibit a preference for the conduction of negative charges are referred to as n-type.

Where it is intended that the charge-generation layer be exposed to actinic radiation through the charge-transport layer, it is preferred that the charge-transport layer have little or no absorption in the region of the electromagnetic spectrum to which the charge-generation layer responds, thus permitting the maximum amount of actinic radiation to reach the charge-generation layer. Where the charge-transport layer is not in the path of exposure, this consideration does not apply.

In addition to the essential charge-generation and charge-transport layers, the multi-active photoconductive insulating elements of this invention can contain various optional layers, such as subbing layers, overcoat layers, barrier layers, and the like.

In certain instances, it is advantageous to utilize one or more adhesive interlayers between the conducting substrate and the active layers in order to improve adhesion to the conducting substrate and/or to act as an electrical barrier layer as described in Dessauer, U.S. Pat. No. 2,940,348. Such interlayers, if used, typically have a dry thickness in the range of about 0.1 to about 5 microns. Typical materials which may be used include film-forming polymers such as cellulose nitrate, polyesters, copolymers of poly(vinyl pyrrolidone) and vinyl acetate, and various vinylidene chloride-containing polymers including two, three and four component polymers prepared from a polymerizable blend of monomers or prepolymers containing at least 60 percent by weight of vinylidene chloride. A partial list of representative vinylidene chloride-containing polymers includes vinylidene chloride-methyl methacrylate-itaconic acid terpolymers as disclosed in U.S. Pat. No. 3,143,421. Various vinylidene chloride containing hydrosol tetrapolymers which may be used include tetrapolymers of vinylidene chloride, methyl acrylate, acrylonitrile, and acrylic acid as disclosed in U.S. Pat. No. 3,640,708. A partial listing of other useful vinylidene chloride-containing copolymers includes poly(vinylidene chloride-methyl acrylate), poly(vinylidene chloride-methacrylonitrile), poly(vinylidene chloride-acrylonitrile), and poly(vinylidene chloride-acrylonitrile-methyl acrylate). Other useful materials include the so-called "tergels" which are described in Nadeau et al, U.S. Pat. No. 3,501,301.

One especially useful interlayer material which may be employed in the multi-active element of the invention is a hydrophobic film-forming polymer or copolymer free from any acid-containing group, such as a carboxyl group, prepared from a blend of monomers or prepolymers, each of said monomers or prepolymers containing one or more polymerizable ethylenically unsaturated groups. A partial listing of such useful materials includes many of the above-mentioned copolymers, and, in addition, the following polymers: copolymers of polyvinylpyrrolidone and vinyl acetate, poly(-vinylidene chloride-methyl methacrylate), and the like.

Optional overcoat layers may be used in the present invention, if desired. For example, to improve surface hardness and resistance to abrasion, the surface layer of the multi-active element of the invention may be coated with one or more electrically insulating, organic polymer coatings or electrically insulating, inorganic coatings. A number of such coatings are well known in the art and, accordingly, extended discussion thereof is unnecessary. Typical useful overcoats are described, for example, in *Research Disclosure*, "Electrophotographic Elements, Materials, and Processes", Volume 109, page 63, Paragraph V, May, 1973, which is incorporated by reference herein.

The essential component of the charge-generation layer in the novel photoconductive elements of this invention is 3-methyl PPC. In preparing the novel multi-active photoconductive insulating elements of this invention, the 3-methyl PPC can be deposited by any one of a variety of suitable techniques. For example, it can be deposited in the form of a binder-free layer by techniques such as vacuum deposition or sputtering, or it can be dispersed in a liquid medium containing a polymeric binder and the dispersion can be coated in the form of a layer of suitable thickness.

As indicated hereinabove, the second of the essential layers of the multi-active photoconductive insulating elements of this invention is a charge-transport layer. This layer comprises a charge-transport material which is an organic photoconductive material that is capable of accepting and transporting injected charge carriers from the charge-generation layer. The organic photoconductive material can be a p-type material, that is a material which is capable of transporting positive charge carriers, or an n-type material, that is a material which is capable of transporting negative charge carriers. The term "organic", as used herein, is intended to refer to both organic and metallo-organic materials.

Illustraive p-type organic photoconductive materials include:

1. carbazole materials including carbazole, N-ethyl carbazole, N-isopropyl carbazole, N-phenyl carbazole, halogenated carbazoles, various polymeric carbazole materials such as poly(vinyl carbazole) halogenated poly(vinyl carbazole), and the like.

2. arylamine-containing materials including monoarylamines diarylamines, triarylamines, as well as polymeric arylamines. A partial listing of specific arylamine organic photoconductors includes the particular non-polymeric triphenylamines illustrated in Klupfel et al, U.S. Pat. No. 3,180,730 issued Apr. 27, 1965; the polymeric triarylamines described in Fox U.S. Pat. No. 3,240,597 issued Mar. 15, 1966; the triarylamines having at least one of the aryl radicals substituted by either a vinyl radical or a vinylene radical having at least one active hydrogen-containing group as described in Brantly et al, U.S. Pat. No. 3,567,450 issued Mar. 2, 1971; the triarylamines in which at least one of the aryl radicals is substituted by an active hydrogen-containing group as described in Brantly et al, U.S. Pat. No. 3,658,520 issued Apr. 25, 1972; and tritolylamine.

3. polyarylalkane materials of the type described in Noe et al, U.S. Pat. No. 3,274,000 issued Sept. 20, 1966; Wilson, U.S. Pat. No. 3,542,547 issued Nov. 24, 1970; Seus et al, U.S. Pat. No. 3,542,544 issued Nov. 24, 1970, and in Rule et al, U.S. Pat. No. 3,615,402 issued Oct. 26, 1971. Preferred polyarylalkane photoconductors can be represented by the formula:

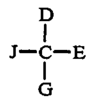

wherein D and G, which may be the same or different, represent aryl groups and J and E, which may be the same or different, represent a hydrogen atom, an alkyl group, or an aryl group, at least one of D, E and G containing an amino substituent. An especially useful polyarylalkane photoconductor which may be employed as the charge-transport material is a polyarylalkane having the formula noted above wherein J and E represent a hydrogen atom, an aryl group, or a alkyl group and D and G represent substituted aryl groups having as a substituent thereof a group represented by the formula:

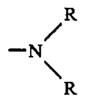

wherein R represents an unsubstituted aryl group such as phenyl or an alkyl substituted aryl such as a tolyl group.

4. strong Lewis base materials such as various aromatic, including aromatically unsaturated heterocyclic-containing, materials which are free of strong electron withdrawing groups. A partial listing of such aromatic Lewis base materials includes tetraphenylpyrene, 1-methylpyrene, perylene, chrysene, anthracene, tetraphene, 2-phenyl naphthalene, azapyrene, fluorene, fluorenone, 1-ethylpyrene, acetyl pyrene, 2,3-benzochrysene, 3,4-benzopyrene, 1-4,-bromopyrene, phenylindole, polyvinyl carbazole, polyvinyl pyrene, polyvinyl tetracene, polyvinyl perylene, and polyvinyl tetraphene.

5. other useful p-type charge-transport materials which may be employed in the present invention are any of the p-type organic photoconductors, including metallo-organo materials, known to be useful in electrophotographic processes, such as any of the organic photoconductive materials described in *Research Disclosure,* Vol. 109, May 1973, pages 61-67, paragraph IV (A) (2) through (13) which are p-type photoconductors.

Illustrative n-type organic photoconductive materials include strong Lewis acids such as organic, including metallo-organic, materials containing one or more aromatic, including aromatically unsaturated heterocyclic, materials bearing an electron withdrawing substituent. These materials are considered useful because of their characteristic electron accepting capability. Typical electron withdrawing substituents include cyano and nitro groups; sulfonate groups; halogens such as chlorine, bromine, and iodine; ketone groups; ester groups; acid anhydride groups; and other acid groups such as carboxyl and quinone groups. A partial listing of such representative n-type aromatic Lewis acid materials having electron withdrawing substituents includes phthalic anhydride, tetrachlorophthalic anhydride, benzil, mellitic anhydride, S-tricyanobenzene, picryl chloride, 2,4-dinitrochlorobenzene, 2,4-dinitrobromobenzene, 4-nitrobiphenyl, 4,4-dinitrobiphenyl, 2,4,6-trinitroanisole, trichlorotrinitrobenzene, trinitro-o-toluene, 4,6-dichloro-1,3-dinitrobenzene, 4,6-dibromo-1,3-dinitrobenzene, P-dinitrobenzene, chloranil, bromanil, 2,4,7-trinitro-9-fluorenone, 2,4,5,7-tetranitrofluorenone, trinitroanthracene, dinitroacridene, tetracyanopyrene, dinitroanthraquinone, and mixtures thereof.

Other useful n-type charge-transport materials which may be employed in the present invention are conventional n-type organic photoconductors, for example, complexes of 2,4,6-trinitro-9-fluorenone and poly(vinyl carbazole) provide useful n-type charge-transport materials. Still other n-type organic, including metallo-organo, photoconductive materials useful as n-type charge-transport materials in the present invention are any of the organic photoconductive materials known to be useful in electrophotographic processes such as any of the materials described in *Research Disclosure,* Vol. 109, May 1973, pages 61-67, paragraph IV (A) (2) through (13) which are n-type photoconductors. The foregoing *Research Disclosure* article is incorporated herein by reference thereto.

Particularly preferred charge-transport materials for the purposes of this invention are the polynuclear tertiary aromatic amines, especially those of the formula:

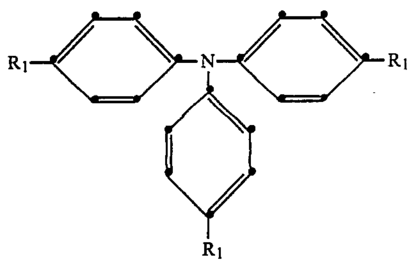

where $R_1$ is hydrogen or alkyl of 1 to 4 carbon atoms, and the aryl alkanes, especially those of the formula:

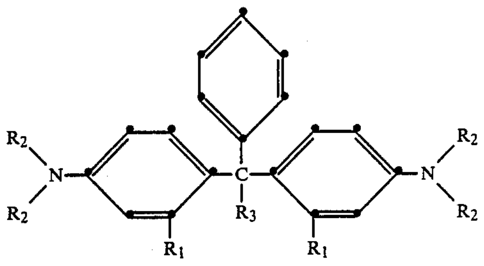

where $R_1$ is hydrogen or alkyl of 1 to 4 carbon atoms, $R_2$ is alkyl of 1 to 4 carbon atoms, and $R_3$ is hydrogen, alkyl of 1 to 4 carbon atoms or phenyl.

Specific illustrative examples of particularly preferred charge-transport materials for use in the photoconductive elements of this invention include:

triphenylamine
tri-p-tolylamine
1,1-bis(4-di-p-tolylaminophenyl)cyclohexane
1,1-bis(4-di-p-tolylaminophenyl)-4-methylcyclohexane
4,4'-benzylidene bis(N,N'-diethyl-m-toluidine)
bis(4-diethylamino)tetraphenylmethane.
1,1-bis(4-[di-4-tolylamino]phenyl)-3-phenylpropane
1,1-bis(4-[di-4-tolylamino]phenyl)-2-phenylethane
1,1-bis(4-[di-4-tolylamino]phenyl)-2-phenylpropane
1,1-bis(4-[di-4-tolylamino]phenyl-3-phenyl-2-propene
bis(4-[di-4-tolylamino]phenyl)phenylmethane
1,1-bis(4-[di-4-tolylamino]-2-methylphenyl-3-phenylpropane
1,1-bis(4-[di-4-tolylamino]phenyl)propane
2,2-bis(4-[di-4-tolylamino]phenyl)butane
1,1-bis(4-[di-4-tolylamino]phenyl)heptane
2,2-bis(4-[di-4-tolylamino]phenyl)-5-(4-nitrobenzoxy)-pentane
and the like.

The charge-transport layer may consist entirely of the charge-transport materials described hereinabove, or, as is more usually the case, the charge-transport layer may contain a mixture of the charge transport material in a suitable film-forming polymeric binder material. The binder material may, if it is an electrically insulating material, help to provide the charge-transport layer with electrical insulating characteristics, and it also serves as a film-forming material useful in (a) coating the charge-transport layer, (b) adhering the charge-transport layer to an adjacent substrate, and (c) providing a smooth, easy to clean, and wear resistant surface. Of course, in instances where the charge-transport material may be conveniently applied without a separate binder, for example, where the charge-transport material is itself a polymeric material, such as a polymeric arylamine or poly(vinyl carbazole), there may be no need to use a separate polymeric binder. However, even in many of these cases, the use of a polymeric binder may enhance desirable physical properties such as adhesion, resistance to cracking, etc.

Where a polymeric binder material is employed in the charge-transport layer, the optimum ratio of charge-transport material to binder material may vary widely depending on the particular polymeric binder(s) and particular charge-transport material(s) employed. In general, it has been found that, when a binder material is employed, useful results are obtained wherein the amount of active charge-transport material contained within the charge-transport layer varies within the range of from about 5 to about 90 weight percent based on the dry weight of the charge-transport layer.

A partial listing of representative materials which may be employed as binders in the charge-transport layer are film-forming polymeric materials having a fairly high dielectric strength and good electrically insulating properties. Such binders include styrene-butadiene copolymers; polyvinyl toluene-styrene copolymers; styrene-alkyd resins; silicon-alkyd resins; soya-alkyd resins; vinylidene chloride-vinyl chloride copolymers; poly(vinylidene chloride); vinylidene chloride-acrylonitrile copolymers; vinyl acetate-vinyl chloride copolymers; poly(vinyl acetals), such as poly(vinyl butyral); nitrated polystyrene; polymethylstyrene; isobutylene polymers; polyesters, such as poly[ethylene-co-alkylenebis(alkyleneoxyaryl)phenylenedicarboxylate]; phenolformaldehyde resins; ketone resins; polyamides; polycarbonates, polythiocarbonates; poly[ethylene-co-isopropylidene-2,2-bis(ethyleneoxyphenylene)-terephthalate]; copolymers of vinyl haloarylates and vinyl acetate such as poly(vinyl-m-bromobenzoate-co-vinyl acetate); chlorinated poly(olefins), such as chlorinated poly(ethylene); etc. Methods of making resins of this type have been described in the prior art, for example, styrene-alkyd resins can be prepared according to the method described in Gerhart U.S. Pat. No. 2,361,019, issued Oct. 24, 1944 and Rust, U.S. Pat. No. 2,258,423, issued Oct. 7, 1941. Suitable resins of the type contemplated for use in the charge-transport layers of the invention are sold under such tradenames as VITEL PE-101, CYMAC, Piccopale 100, Saran F-220, and LEXAN 145. Other types of binders which can be used in charge transport layers include such materials as paraffin, mineral waxes, etc., as well as combinations of binder materials.

In general, it has been found that polymers containing aromatic or heterocyclic groups are most effective as the binder materials for use in the charge-transport layers because these polymers, by virtue of their heterocyclic or aromatic groups, tend to provide little or no interference with the transport of charge carriers through the layer. Heterocyclic or aromatic-containing polymers which are especially useful in p-type charge-transport layers include styrene-containing polymers, bisphenol-A polycarbonate polymers, phenolformaldehyde resins, polyesters such as poly[ethylene-co-isopropylidene-2,2,bis(ethyleneoxyphenylene)]terephthalate, and copolymers of vinyl haloarylates and vinylacetate such as poly(vinyl-m-bromobenzoate-co-vinyl acetate).

The charge-transport layer may also contain other addenda such as leveling agents, surfactants, plasticizers, and the like to enhance or improve various physical properties of the charge-transport layer. In addition, various addenda to modify the electrophotographic response of the element may be incorporated in the charge-transport layer.

The novel multi-active photoconductive insulating elements of the present invention can be prepared by a process comprising the steps of:

(1) depositing on an electrically-conductive support a charge-generation layer, comprising 3-methyl PPC;
(2) overcoating the charge-generation layer with a layer of a liquid composition comprising an organic solvent, a polymeric binder and an organic photoconductive material which is capable of accepting and transporting injected charge-carriers from a charge-generation layer; and
(3) effecting removal of the organic solvent from the element.

Suitable solvents for use in forming the liquid composition can be selected from a wide variety of organic solvents including, for example, ketones such as acetone or methyl ethyl ketone, hydrocarbons such as benzene or toluene, alcohols such as methanol or isopropanol, halogenated alkanes such as dichloromethane or trichloroethane, esters such as ethyl acetate or butyl acetate, ethers such as ethyl ether or tetrahydrofuran, and the like. Mixtures of two or more of the organic solvents can, of course, be utilized and may be advantageous in certain instances.

Removal of the solvent can be accomplished in any suitable manner, such as by merely allowing it to evaporate at room temperature if a relatively volatile solvent had been employed. More typically, solvent removal is effected in a drying process in which the element is subjected to an elevated temperature while exposed to air or an inert gaseous medium. Drying temperatures are typically in the range of from about 30° C. to about 100° C., and drying times in the range of from a few minutes to a few hours.

The liquid composition containing the organic solvent, the organic photoconductive material and the polymeric binder, can be coated over the charge-generation layer by any suitable coating technique, such as, for example, by the use of an extrusion coating hopper, by dip coating, by curtain coating, and the like.

The thickness of the active layers of the multi-active photoconductive insulating elements of this invention can vary widely, as desired. Generally speaking, the charge-transport layer is of much greater thickness than the charge-generation layer. Typically, the charge-generation layer has a thickness in the range of from about 0.005 to about 3.0 microns, and more preferably in the range of from about 0.05 to about 1.0 microns; while the charge-transport layer typically has a thickness in the range of from about 5 to about 100 microns, and more preferably in the range of from about 10 to about 35 microns.

The charge-generation layer can be a binder-free layer consisting solely of 3-methyl PPC. In instances where it is desired to incorporate a binder in the charge-generation layer, the same polymeric materials can be used as have been described herein for use as binders in the charge-transport layer.

Synthesis of 3-methyl PPC can be carried out by methods analogous to well known methods used for synthesizing other perylenes of similar structure. A typical synthesis is as follows:

2-(3-Methylphenyl)ethylamine (59 milliliters; 0.42 mole) was added to a slurry of 3,4,9,10-perylenetetracarboxylic dianhydride (39.2 g; 0.10 mole) in 400 milliliters of a high-boiling solvent such as quinoline or 1-methyl-2-pyrrolidinone. The reaction mixture was refluxed for five hours, filtered, and washed with ethyl alcohol to recover the crude pigment. Purification and crystal ripening was achieved by refluxing the crude material two or three times in the high-boiling solvent, at a concentration of one gram of pigment per ten milliliters of solvent. The purified pigment was collected by filtration, washed thoroughly with alcohol and acetone, and dried under vacuum at 110° C. The yield of black, crystalline pigment was 95 to 97%. IR (KBr): 1,675 and 1,645 centimeters$^{-1}$ (imide carbonyl stretch).

Calculated for $C_{42}H_{30}N_2O_4$: C, 80.5; H, 4.8; N, 4.5; O, 10.2. Found: C, 79.6; H, 5.0; N, 4.4; O, 10.2.

In the photoconductive elements of this invention, an adhesive polymer interlayer is preferably incorporated between the electrically-conductive support and the charge-generation layer. It is particularly preferred to utilize as the adhesive polymer an acrylonitrile copolymer as described in Staudenmayer et al, U.S. Pat. No. 4,578,333.

The invention is further illustrated by the following examples of its practice.

EXAMPLE 1

A multi-active photoconductive insulating element was prepared utilizing 3-methyl PPC as the charge-generating agent and 1,1-bis(4-di-p-tolylaminophenyl)-4-methylcyclohexane as the charge-transport agent. The support for the element consisted of a poly(ethylene terephthalate) film coated with a conductive nickel layer that was overcoated with an adhesive interlayer comprised of poly[acrylonitrile-co-vinylidene chloride (15/85)]. To form the charge-generation layer, a 0.5 micron thick layer of 3-methyl PPC was vacuum-deposited over the interlayer. To form the charge-transport layer, a mixture of 60% by weight bisphenol-A-polycarbonate and 40% by weight 1,1-bis(4-[di-4-tolylamino]phenyl)-3-phenylpropane was dissolved in dichloromethane to form a solution of 11% by weight solids; the solution was coated over the charge-generation layer in an amount providing a dry thickness of 24 microns; and the element was dried at 85° C. for 15 minutes.

The element prepared in the manner described above was tested for electrophotographic speed and found to require an exposure of only 2.2 ergs/cm$^2$ at 630 nm to discharge from 500 to 100 volts. This is an exceptionally high speed, exceeding even the very high speeds reported in the working examples of Borsenberger et al, U.S. Pat. No. 4,578,334.

EXAMPLE 2

A series of multi-active photoconductive insulating elements was prepared using various perylene dicarboximides as the charge-generating agent and tri-p-tolylamine as the charge-transport agent, and each element was evaluated to determine its sensitivity in the far red region of the spectrum. The elements were prepared in a similar manner to that described in Example 1 above, except that the polymeric binder utilized in the charge-transport layer was a polyester formed from 4,4'-(2-norbornylidene)diphenol and a mixture of 40 mole % azelaic acid and 60 mole % terephthalic acid, and various solvents were employed in forming the charge-transport layer as indicated below.

The perylene compounds evaluated were of the following general formula in which R is defined below.

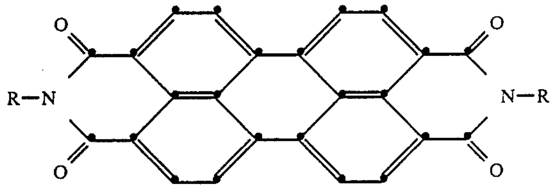

| Perylene Compound | Definition of R |
| --- | --- |
| 3-methyl PPC | 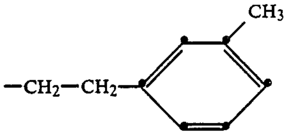 |
| A | 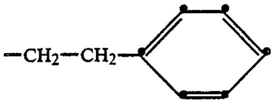 |
| B | 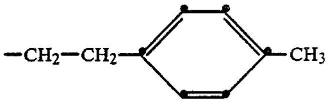 |
| C | 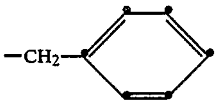 |
| D | 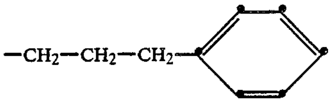 |
| E | 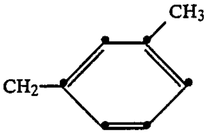 |
| F | 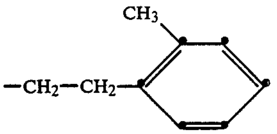 |
| G | 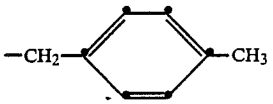 |
| H | 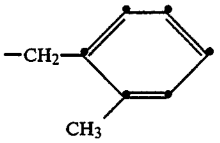 |

The solvents utilized were as follows:

Solvent 1—mixture of 60% by weight dichloromethane and 40% by weight 1,1,2-trichloroethane.

Solvent 2—dichloromethane.

Solvent 3—dioxane.

To evaluate sensitivity in the far red region of the spectrum, the optical density at 675 nm was measured with a Diano spectrophotometer with diffuse collection geometry and converted to a net optical density by subtracting 0.4, which represents the optical density of the nickel conducting layer.

The results obtained are summarized in the following table:

| Test No. | Perylene Compound | Organic Solvent | Net Optical Density |
|---|---|---|---|
| 1-A | 3-methyl PPC | Solvent 1 | 0.42 |
| 1-B | 3-methyl PPC | Solvent 2 | 0.48 |
| 1-C | 3-methyl PPC | Solvent 3 | 0.42 |
| 2-A | A | Solvent 1 | 0.03 |
| 2-B | A | Solvent 2 | 0.09 |
| 2-C | A | Solvent 3 | 0.03 |
| 3-A | B | Solvent 1 | 0.09 |
| 3-B | B | Solvent 2 | 0.06 |
| 3-C | B | Solvent 3 | 0 |
| 4-A | C | Solvent 1 | 0 |
| 4-B | C | Solvent 2 | 0.03 |
| 4-C | C | Solvent 3 | 0.09 |
| 5-A | D | Solvent 2 | 0 |
| 5-B | D | Solvent 3 | 0 |
| 6-A | E | Solvent 1 | 0 |
| 6-B | E | Solvent 2 | 0 |
| 6-C | E | Solvent 3 | 0 |
| 7-A | F | Solvent 1 | 0 |
| 7-B | F | Solvent 2 | 0.02 |
| 7-C | F | Solvent 3 | 0 |
| 8-A | G | Solvent 1 | 0 |
| 8-B | G | Solvent 2 | 0 |
| 9 | H | Solvent 2 | 0 |

As indicated by the experimental results reported above, only the novel perylene compound of this invention, namely 3-methyl PPC, exhibits significant absorption at 675 nm. This is surprising, considering that there are only slight structural differences between 3-methyl PPC and the other perylene compounds evaluated. Thus, the specific structure of 3-methyl PPC is critical with respect to the important property of far red sensitivity. Comparing the structures of perylenes A to H with the structure of 3-methyl PPC, it is apparent that both the presence of a methyl substituent at the 3-position on the phenyl radical and the ethylene linkage joining the phenyl radical to the nitrogen atom are critical structural features.

The novel multi-active photoconductive insulating elements of this invention provide a unique combination of desirable properties not heretofore attainable in this art, including very high electrophotographic speed, sensitivity extending across the visible spectrum and into the far red, high quantum efficiency, low electrical noise, low dark-decay, and ability to accept a high surface charge. Because of their sensitivity in the far red, they are especially useful in electronic printers which utilize, as exposure devices, lasers or light emitting diodes that emit in the far red.

The invention has been described in detail with particular reference to preferred embodiments thereof, but it will be understood that variations and modifications can be effected within the spirit and scope of the invention.

We claim:

1. As a composition of matter, the compound N,N'-bis[2-(3-methylphenyl)ethyl]-perylene-3,4:9,10-bis(-dicarboximide).

* * * * *